United States Patent
Baer et al.

(10) Patent No.: US 9,790,331 B2
(45) Date of Patent: Oct. 17, 2017

(54) PROCESS FOR PREPARING A BIO-RESORBABLE POLYESTER IN THE FORM OF A POWDER

(71) Applicants: Hans Baer, Michelstadt (DE); Felix Hofmann, Darmstadt (DE); Silke Schminke, Zwingenberg (DE); Julian Blaesy, Weiterstadt (DE); Isabel Wahl, Kahl am Main (DE)

(72) Inventors: Hans Baer, Michelstadt (DE); Felix Hofmann, Darmstadt (DE); Silke Schminke, Zwingenberg (DE); Julian Blaesy, Weiterstadt (DE); Isabel Wahl, Kahl am Main (DE)

(73) Assignee: Evonik Roehm GmbH, Darmstadt (DE)

(*) Notice: Subject to any disclaimer, the term of this patent is extended or adjusted under 35 U.S.C. 154(b) by 0 days.

(21) Appl. No.: 14/912,302

(22) PCT Filed: Aug. 29, 2013

(86) PCT No.: PCT/EP2013/067872
§ 371 (c)(1),
(2) Date: Feb. 16, 2016

(87) PCT Pub. No.: WO2015/028060
PCT Pub. Date: Mar. 5, 2015

(65) Prior Publication Data
US 2016/0208057 A1    Jul. 21, 2016

(51) Int. Cl.
C08J 3/14    (2006.01)
C08J 3/12    (2006.01)
C08G 63/90   (2006.01)
A61L 27/18   (2006.01)
A61L 31/06   (2006.01)
A61K 47/34   (2017.01)
A61L 31/14   (2006.01)
C08G 63/08   (2006.01)

(52) U.S. Cl.
CPC ............. *C08J 3/14* (2013.01); *A61K 47/34* (2013.01); *A61L 27/18* (2013.01); *A61L 31/06* (2013.01); *A61L 31/148* (2013.01); *C08G 63/08* (2013.01); *C08G 63/90* (2013.01); *C08J 3/12* (2013.01); *C08J 2367/04* (2013.01)

(58) Field of Classification Search
CPC . C08J 3/12; C08J 3/14; C08J 2367/04; A61K 47/34; A61L 27/18; A61L 31/06; A61L 31/148; C08G 63/08; C08G 63/90
See application file for complete search history.

(56) References Cited

U.S. PATENT DOCUMENTS

| | | | |
|---|---|---|---|
| 4,810,775 A * | 3/1989 | Bendix | A61L 27/18 210/768 |
| 2009/0104274 A1* | 4/2009 | Khopade | A61K 9/5031 424/490 |
| 2010/0137550 A1 | 6/2010 | Enderle et al. | |
| 2011/0144301 A1 | 6/2011 | Enderle et al. | |
| 2011/0288267 A2* | 11/2011 | Enderle | C08G 63/90 528/354 |
| 2013/0090401 A1* | 4/2013 | Hashaikeh | A61L 27/56 521/182 |

FOREIGN PATENT DOCUMENTS

| | | |
|---|---|---|
| EP | 2 455 414 A1 | 5/2012 |
| EP | 2 455 415 A1 | 5/2012 |
| WO | 2007 088135 A1 | 8/2007 |
| WO | WO2010/110425 A1 | 3/2010 |

OTHER PUBLICATIONS

Hyon, Suong Hyn. "Biodegradable poly (lactic acid) microspheres for drug delivery systems." Yonsei medical journal 41.6 (2000): 720-734.*
Phattanaphibul, Thittikorn, et al. "Preparing biodegradable PLA for powder-based rapid prototyping." Proceedings of the 8th APIEMS conference. Taiwan. 2007.*
International Search Report and Written Opinion Issued Mar. 21, 2014, in PCT/EP2013/067872 Filed Aug. 29, 2013.

* cited by examiner

*Primary Examiner* — Nicholas Hill
(74) *Attorney, Agent, or Firm* — Oblon, McClelland, Maier & Neustadt, L.L.P.

(57) ABSTRACT

The invention refers to a Process for preparing a bio-resorbable polyester the form of a powder with a bulk density of 0.3 g/ml or more, a tapped density of 0.4 g/ml or more and a specific surface area of 2.0 m²/g or less comprising the steps a. dissolving a bio-resorbable polyester in a first solvent to form a polymer solution, b. contacting the polymer solution with a second solvent which is a non-solvent for the bioresorbable polyester and which is mainly water to result the precipitation of the bio-resorbable polyester in the form of a wet polymer mass, c. pre-drying the wet polymer mass at a temperature below the $T_{gO}$ of the bio-resorbable polyester, d. comminuting the pre-dried polymer mass to polymer particles with a size below 10 mm, e. drying the comminuted polymer particles below the $T_{gO}$ of the bio-resorbable polyester to a residual water content of 1% or less by weight/weight, f. post-treatment of the polymer particles from step e at a temperature in the range from the $T_{gO}$ to the $T_{gE}$ of the bio-resorbable polyester, g. comminuting the polymer particles from step f to a powder with a particle size of $d_{50}$ of 1-300 µm and $d_{90}$ of more than 30 and up to 3000 µm.

12 Claims, No Drawings

PROCESS FOR PREPARING A BIO-RESORBABLE POLYESTER IN THE FORM OF A POWDER

TECHNICAL BACKGROUND

U.S. Pat. No. 5,007,923 describes crystalline copolyesters of amorphous lactide/glycolide and dioxanone.

U.S. Pat. No. 6,706,854 describes a process for preparing resorbable polyesters by mass polymerization.

US2010/0137550A1 describes a method and device for cleaning absorptive or resorbable polyester. The process for purifying a resorbable polyester is comprising the steps of dissolving the resorbable polyester in a first solvent to form a polymer solution, intimately contacting the polymer solution with a second solvent under the action of high shear forces in a turbulent shear field to form a polymer suspension, wherein the second solvent is a non-solvent for the resorbable polyester and is unlimitedly miscible with the first solvent, conveying the polymer suspension onto or into a rotating cylindrical screen body and drying the polymer mass.

Problem and Solution

Bio-resorbable polyesters are well known in the art for preparing bio-degradable pharmaceutical active ingredient containing dosage forms suitable for in-situ sustained release applications in the human body or in an animal body. Bio-resorbable polyesters are also used for preparing bio-degradable surgical articles, such as filaments, rods, stents or prostheses. The preparation of controlled release articles or medical devices usually requires certain specification of bio-resorbable polyesters raw material which is usually delivered in the form of a powder. Although several methods for preparing Bio-resorbable polyesters are known, it is often difficult to meet certain specifications. A general problem is the formation of microscopic pores in the material during the drying processes probably induced by water evaporation. Such pores are unwanted in the further processing. The inventors describe herein a process as claimed for preparing bio-resorbable polyesters in which the formation of microscopic pores in powder material is remarkably reduced. This is beneficial since the further processing of the bio-resorbable polyesters for instance by injection molding to surgery articles such as stents or other implantable articles becomes more reproducible and reliable. The amount of articles out of the specification in production processes can be reduced.

DEFINITIONS AND ANALYTICAL METHODS

Bulk/Tapped Density

The determinations of the bulk/tapped density are performed according to the United States Pharmacopeia 36 (USP) chapter <616> and European Pharmacopeia (EP) chapter 2.9.15. The interparticulate interactions that influence the bulk properties of a powder are also the interactions that interfere with the powder flow, a comparison of the bulk and tapped densities can give a measure of the relative importance of these interactions in a given powder. The bulk density of the powder "as poured" or passively filled into a measuring vessel. The tapped density is a limiting density attained after "tapping down," usually in a device that lifts and drops a volumetric measuring cylinder containing the powder a fixed distance.

Bulk Density

The bulk density is determined by measuring the volume of a known mass of powder sample that has been passed without agglomerates into a graduated cylinder (Method I) or through a volume-measuring apparatus into a cap (Method II). For the purposes of the described invention only Method I was utilized for bulk density determinations.

Tapped Density

The tapped density is achieved by mechanically tapping a measuring cylinder containing a powder sample. After observing the initial volume, the cylinder is mechanically tapped, and volume readings are taken until only a little volume change is observed. The mechanical tapping is achieved by raising the cylinder and allowing it to drop under its own weight a specified distance.

Specific Surface Area

The determination of the specific surface area is preferably performed according to the United States Pharmacopeia 36 (USP) chapter <846> and European Pharmacopeia 7.0 (EP) chapter 2.9.26. The specific surface area is determined utilizing a specific surface area detection equipment (e.g. Quantachrome Nova 2000e BET).

Inherent Viscosity (IV)

The determination of the inherent viscosity is preferably performed in a Ubbelohde viscometer of type 0c at 25±0.1° C. utilizing a sample concentration of 0.1% dissolved in chloroform.

Water Content Determination

The water content may be determined coulometric by the Karl Fischer method or gravimetric by the loss on drying method.

Karl Fischer Method/Coulometric Titration

The determination of the water content may be performed according to the United States Pharmacopeia 36 (USP) chapter <921> Method Ic and European Pharmacopeia 7.0 (EP) chapter 2.5.32. The Karl Fischer (KF) reaction is used in the coulometric determination of water. Iodine, however, is not added in the form of a volumetric solution but is produced in an iodide-containing solution by anodic oxidation. In the KF oven method, the test substance is heated in a tightly sealed vessel in an oven. The water driven off from the sample is transported into the titration cell with the help of a stream of dry nitrogen gas; there it is determined, usually by means of coulometric KF titration. As reference a standard lactose samples are utilized. Because the sample itself remains in the vessel and only the water enters the titration cell, secondary reactions and matrix effects can be ruled out.

Gravimetric/Loss on Drying (LOD)

The water content may be performed may be determined according to the United States Pharmacopeia 36 (USP) chapter <921> Method III and procedure for chemicals—proceed as directed in the individual monograph preparing the chemical as directed under Loss on Drying (LOD) <731> and also according European Pharmacopeia 7.0 (EP) chapter 2.2.32. However, this method suffers from the drawback that it determines not only the water content, but also other volatile constituents in the sample.

Particle Size Distribution

The particle size may be determined by light diffraction (laser scattering) or by image analysis.

Specific Surface Area

The specific surface area is preferably determined according to the United States Pharmacopeia 36 (USP) chapter <846> and European Pharmacopeia 7.0 (EP) chapter 2.9.26. The specific surface area is determined utilizing a specific surface area detection equipment (e.g. Quantachrome Nova 2000e BET). The specific surface area was measured using the multi-point and single-point determination using the static-volumetric method (Method II). Prior to the measurement the sample is degassed at 20° C. and vacuum is applied.

Inherent Viscosity IV

The Inherent viscosity (IV) is preferably determined in an Ubbelohde viscometer of type 0c at 25±0.1° C. utilizing a sample concentration of 0.1% dissolved in chloroform.

Glass Transition Temperatures

The different Glass transition temperatures are preferably determined according to the United States Pharmacopeia 36 (USP) chapter <891>, European Pharmacopeia 7.0 (EP) chapter 2.2.34 and according to DIN 53765:1994-03 (D).
$T_g$=glass transition temperature
$T_{gO}$=glass transition onset temperature
$T_{gO}^E$=glass transition extrapolated onset temperature
$T_{gE}$=Glass transition end temperature
$T_{gE}^E$=Glass transition extrapolated end temperature Glass Transition Temperatures of Bio-Resorbable Polyesters Table 1 summarizes the different glass transition temperatures of a number of widely used bio-resorbable polyesters of the poly(D,L-lactide) and poly(D,L-lactide-co-glycolide) type which are commercially available under the Trade name RESOMER®.

The bio-resorbable polyester is preferably selected from lactic acid polymers or copolymers synthesized from monomer components or from a mixture of monomer components selected from the group consisting of a) to l):
a) D- and L-lactide,
b) L-lactide and glycolide,
c) D,L-lactide and glycolide,
d) L-lactide and epsilon-caprolactone,
e) L-lactide and dioxanone,
f) L-lactide and trimethylene carbonate,
g) L-lactide. D-lactide, meso-lactide or D,L-lactide,
h) L-lactide,
i) DL-lactide,
j) statistically distributed monomer units of L-lactide, D-lactide, meso-lactide or DL-lactide and epsilon caprolactone,
k) statistically distributed monomer units of L-lactide. D-lactide, meso-lactide or DL-lactide and dioxanone,
l) statistically distributed monomer units of L-lactide. D-lactide, meso-lactide or DL-lactide and trimethylene carbonate.

These kind of lactic acid polymers or copolymers are biodegradable polyester polymers and well known in the art for example from EP1468035, U.S. Pat. No. 6,706,854, WO2007/009919A2, EP1907023A, EP2263707A,

TABLE 1

Glass Transition Temperatures of bio-resorbable polyesters of the poly(D,L-lactide) and poly(D,L-lactide-co-glycolide) type

| RESOMER® | Polymer Composition | IV (dL/g) | End group | $T_{gO}$ [° C.] | $T_{gO}^E$ [° C.] | $T_g$ [° C.] | $T_{gE}^E$ [° C.] | $T_{gE}$ [° C.] |
|---|---|---|---|---|---|---|---|---|
| R202 S | Poly(D,L-lactide) | 0.22 | Ester | 34.3 | 37.8 | 40.3 | 43.2 | 48.3 |
| R202 H | Poly(D,L-lactide) | 0.23 | Acid | 44.0 | 47.0 | 48.8 | 50.5 | 55.4 |
| R203 S | Poly(D,L-lactide) | 0.32 | Ester | 39.1 | 44.0 | 46.2 | 48.5 | 54.4 |
| R203 H | Poly(D,L-lactide) | 0.33 | Acid | 46.1 | 48.9 | 50.5 | 52.1 | 57.5 |
| RG 502 | Poly(D,L-lactide-co-glycolide) 50:50 | 0.22 | Ester | 36.6 | 39.7 | 41.4 | 43.1 | 48.2 |
| RG 502 H | Poly(D,L-lactide-co-glycolide) 50:50 | 0.20 | Acid | 38.2 | 42.6 | 44.1 | 45.7 | 51.2 |
| RG 503 | Poly(D,L-lactide-co-glycolide) 50:50 | 0.43 | Ester | 41.8 | 44.9 | 46.5 | 48.1 | 53.2 |
| RG 503 H | Poly(D,L-lactide-co-glycolide) 50:50 | 0.35 | Acid | 40.6 | 44.9 | 46.6 | 48.3 | 54.6 |
| RG 504 | Poly(D,L-lactide-co-glycolide) 50:50 | 0.59 | Ester | 41.9 | 46.1 | 48.1 | 50.0 | 56.2 |
| RG 504 H | Poly(D,L-lactide-co-glycolide) 50:50 | 0.59 | Acid | 41.1 | 45.6 | 47.6 | 49.6 | 56.2 |
| RG 653 H | Poly(D,L-lactide-co-glycolide) 65:35 | 0.37 | Acid | 39.2 | 45.9 | 47.8 | 49.8 | 57.0 |
| RG 752 H | Poly(D,L-lactide-co-glycolide) 75:25 | 0.20 | Acid | 38.8 | 44.1 | 46.0 | 48.0 | 53.8 |
| RG 752 S | Poly(D,L-lactide-co-glycolide) 75:25 | 0.19 | Ester | 31.0 | 33.9 | 36.5 | 39.1 | 44.7 |
| RG 750 S | Poly(D,L-lactide-co-glycolide) 75:25 | 1.11 | Ester | 45.8 | 49.3 | 51.1 | 52.9 | 59.1 |

Bio-resorbable Polyester

A bio-resorbable polyester in the sense of the invention is preferably a lactic acid polymer or a lactic acid based polymer in a broad sense, for instance a homopolymer or copolymer based for instance on lactide (L-lactide, D-lactide, DL-lactide, mesolactide), glycolide, epsilon caprolactone, dioxanone, trimethylene carbonate, delta-valerolactone, gamma-butyrolactone and similar polymerizable heterocycles. These polymers can either be composed of one or else of a plurality of different monomer modules in the polymer chain such as for instance ethylene glycol. Bio-resorbable polyesters are raw materials which are widely used for the production of bio-resorbable surgical implants and also as a pharmaceutical carrier for the formulation of parenteral release systems.

The bio-resorbable polyester can be a polylactic acid, a polyglycolic acid, a poly-caprolactone, a lactic acid-glycolic acid copolymer, a lactic acid-glycolic acid-polyethylene blockcopolymer, a lactic acid-glycolic acid-caprolactone terpolymer, a lactic acid-caprolactone copolymer, a poly dioxanone or a lactic acid-trimethylene carbonate copolymer or any blend of the fore mentioned polymers.

EP2147036, EPO427185 or U.S. Pat. No. 5,610,266. Depending on the production process the polymers may have different end groups such as ester or acid end groups.

Preferably the bio-resorbable polyester is a poly(D,L-lactide-co-glycolide) copolymer preferably with an inherent viscosity IV from 0.1-2.0, 0.12-1.2, 0.14-1.0, 0.16-0.44, 0.16-0.24 [dL/g].

A preferred bio-resorbable polyester is a poly(D,L-lactide-co-glycolide) copolymer with a proportion of D,L-lactide to glycolide in the poly(D,L-lactide-co-glycolide) copolymer is from 80:20 to 20:80, 70:30 to 30:70, 60:40 to 40:60 parts by weight.

A preferred bio-resorbable polyester are RESOMER® RG 502 or RESOMER® RG 502 H which are a poly(D,L-lactide-co-glycolide/50:50) copolymers with anInherent viscosity IV from 0.16-0.44 or 0.16-0.24 [dL/g].

The term "bio-resorbable" in "bio-resorbable polyester" means that the polyester, which is preferably a lactid acid based polymer, is after implantation or injection in the human body or in the body of an animal in contact with the body fluids broken down into oligomers in a slow hydrolytic reaction. Hydrolysis end products such as lactic acid or glycolic acid are metabolized into carbon dioxide and water. Other exchangeable expressions for the term "bio-resorbable polyester" which are often used are "resorbable polyester", "bio-degradable polyester" or "adsorptive polyester".

DETAILED DESCRIPTION OF THE INVENTION

The invention refers to a process for preparing a bio-resorbable polyester the form of a powder with a bulk density of 0.3 g/ml or more, 0.35 g/ml or more, 0.4 g/ml or more, 0.45 g/ml or more, 0.5 g/ml or more, preferably from 0.3 to 0.75, 0.35 to 0.65, 0.4 to 0.6, 0.4-0.45, 0.5-0.6.

The invention refers to a process for preparing a bio-resorbable polyester the form of a powder with a tapped density of 0.4 g/ml or more, 0.5 g/ml or more, preferably from 0.4 to 0.75, 0.45 to 0.65, 0.5 to 0.55, 0.55-0.7.

The invention refers to a process for preparing a bio-resorbable polyester in the form of a powder with a specific surface area 2.0 m$^2$/g or less, 1.5 m$^2$/g or less, 1.0 m$^2$/g or less, 0.01-2 m$^2$/g, 0.1-1 m$^2$/g.

The Process Comprises the Steps a to g
Step a:
A bio-resorbable polyester is dissolved in a first solvent, preferably an organic solvent, for instance hexane or acetone, to form a polymer solution.
Step b:
The polymer solution from step a is contacted with a second solvent which is a non-solvent for the bio-resorbable polyester and which comprises water, preferably mainly water, to result the precipitation of the bio-resorbable polyester in the form of a wet polymer mass. Most of the second solvent in excess may be removed by filtration. After filtration a wet or an aqueous polymer mass remains. The polymer mass may still show a water residual content of around 50% or more, 60% or more, 70% or more, 80% or more, 90% or more, 50-90%, 60-80% by weight/weight (w/w). The wet polymer mass usually has the form of a lump, a clot or a nugget. The terms "comprises water" or "comprises mainly water" shall mean that the second solvent is either 100% water, or a mixture of more than 50, more than 60, more than 70, more than 80 or more than 90% water with water soluble solvents such as ethanol or isopropanol. Preferably the second solvent is water.
Step c:
In step c the wet polymer mass is pre-dried to a consistence that allows the comminution of the polymer mass in step d. The wet polymer mass is therefore dried at a temperature below the $T_{gO}$, preferably at a temperature in the range from 15° C. up to below the $T_{gO}$ of the bio-resorbable polyester, preferably in a range from 18-36° C. The drying temperatures refer to the product temperature which is herein identical to the so called product bed temperature. Before step c the polymer mass may show a water residual content of around 50% or more, 60% or more, 70% or more, 80% or more, 90% or more, 50% or more up to 90%, 60-80% (w/w). In step c the wet polymer mass, which may be in the form of a lump, a clot, an agglomerate or a nugget is dried more or less irregularly from the outside while there is more moisture left in the inside. However this is sufficient to change the morphology in so far as it becomes possible to break the polymer mass down to particles in step d).

A consistence that allows the comminution of the polymer mass may be achieved when the residual water content of the wet polymer mass measured as LOD is reduced to about 30 to 70, 30-60, 35-50% by weight/weight.

A consistence that allows the comminution of the polymer mass may be achieved after 30 to 150, 60 to 120 min of pre-drying.

Step c is preferably performed in a fluidized bed drying equipment. In this case the drying temperature refers to the product bed temperature.
Step d:
The dried polymer mass is comminuted to polymer particles with a size below 10 mm, preferably below 5 mm, below 3 mm, below 2 mm or from 0.5 to 10, 1 to 5, 1.5-4 mm. Comminution can be performed for instance by passing the dried polymer mass, manually or utilizing a sieving apparatus, through one or more sieves. Usually the particles gained in this step are of irregular form. The comminution has the purpose to enlarge the surface area which eases further drying.
Step e
In step e the comminuted polymer particles from step f are further dried at a temperature below the $T_{gO}$, preferably at a temperature in the range from 15° C. up to below the $T_{gO}$ of the bio-resorbable polyester to a residual water content of 1% or less, 0.8% or less, 0.5-1%, more than 0.3% up to 1%, more than 0.5 and up to 1% by weight/weight (w/w). Step e may be carried out for around 60 to 240, preferably 120 to 200 min.
Step f:
Post-treatment or post-drying step e is considered to be essential for the reduction, removal or avoidance of the formation of microscopic pores within the bio-resorbable polyester powder which is to be produced in step f.

The polymer particles are post treated at a temperature in the range from the $T_{gO}$ to the $T_{gE}$ or more preferred from the $T_{gO}$ to the $T_{gE}^E$ or most preferred from the $T_{gO}^E$ to the $T_{gE}^E$ of the bio-resorbable polyester. The drying temperatures refer to the product temperature which is herein identical to the so called product bed temperature.

The post treatment time may be around 5 to 120, 10 to 90 min, 15 to 60 min at the post treatment temperature. The product yield before milling in step f may be 75% or more. Preferably, the polymer particles in step f are post treated at a temperature in the range from the $T_{gO}^E$ to the $T_{gE}^E$ of the bio-resorbable polyester. In this temperature range the product yield before milling is usually 80% or more, preferably 90% or more, and the tendency of the particles to form aggregates is lower than when post-treatment temperatures above $T_{gE}^E$ are applied. A post-treatment above the $T_{gE}$ temperature usually results in a strong clotting or sintering of the polymer particles which in most cases leads to unacceptable end products.

In case of occurring larger bio-resorbable polyester lumps, clots, agglomerates or nuggets the material will be discharged and granulated through a 10 mm, preferably 5 mm, 3 mm, 2 mm screen (e.g. manually or utilizing a sieving apparatus).

The polymer particles in step f are dried to a residual water content of 0.5% or less, less than 0.5%, 0.45% or less, 0.4% or less, 0.1-0.4%, 0.15 to 0.3% (w/w). Step e is preferably performed in a fluidized bed drying equipment. In this case the post treatment temperature refers to the product bed temperature.
Step g:
The particles from step f have become finer after the post-treatment but are still too irregular and thus must be brought into the form of more unique powder particles.

The dried polymer particles are comminuted to a powder preferably with a particle size of with a $d_{50}$ of 1 to 300 μm and a $d_{90}$ of more than 30 and up to 3000, $d_{50}$ of 10 to 100

μm and $d_{90}$ of more than 50 and up to 1000 μm or less, $d_{50}$ of 1 to 30 and $d_{90}$ of more than 30 and up to 60 μm. The $d_{10}$ value is preferably less than 100, less than 10, for instance 1 to less than 10 μm.

Comminution may be performed by a powder mill, preferably a jet mill avoiding too much energy uptake of the bio-resorbable polyester to temperatures above $T_{gO}$. The powder particles are usually of a regular spherical shape.

Bio-resorbable Polyester

The process according to the invention provides a bio-resorbable polyester in the form of a powder preferably with a particle size with a $d_{50}$ of 1 to 300 μm and $d_{90}$ of more than 30 and up to 3000, $d_{50}$ of 10 to 100 μm and $d_{90}$ of more than 50 and up to 1000 μm or less, $d_{50}$ of 1 to 30 and $d_{90}$ of more than 30 and up to 60 μm. The $d_{10}$ value may be less than 100, less than 10, for instance 1 to less than 10 μm. A preferred bio-resorbable polyester is a lactid acid polymer.

The $d_{10}$ value is always lower than the $d_{50}$ value. The $d_{50}$ value is always lower than the $d_{90}$ value. Thus the $d_{10}$, the $d_{50}$ and $d_{90}$ ranges mentioned here are allowed to overlap without being partially identical, illogical or illegitimate since in every case of a particle distribution the $d_{10}$ value is lower than the $d_{50}$ value and the $d_{50}$ value is lower than the $d_{90}$ value. In the case of an overlapping of the $d_{50}$ and $d_{90}$ ranges, the $d_{50}$ value is lower than the $d_{90}$ value. In the case of an overlapping of the $d_{10}$ the $d_{50}$ or the $d_{90}$ ranges, the $d_{10}$ value is lower than the $d_{50}$ value and the $d_{50}$ value is lower than the $d_{90}$ value.

Use

The bio-resorbable polyester may be used for preparing a bio-resorbable pharmaceutical active ingredient containing dosage form suitable for an in-situ sustained release application in the human body or in an animal body.

The bio-resorbable polyester may be used for preparing a bio-resorbable surgical article, such as filament, a rod, a stent or prostheses.

EXAMPLES

Bulk Density

The bulk density was determined according to the United States Pharmacopeia 36 (USP) chapter <616> and European Pharmacopeia (EP) chapter 2.9.15 by measuring the volume of a known mass of powder sample that has been passed without agglomerates into a graduated cylinder (Method I).

Into a 100 ml (readable to 1 mm) cylinder, without compacting, an apparent volume between 50 ml and 100 ml is introduced, weighted [M] with 0.1% accuracy. Carefully the powder sample leveled without compacting, if necessary, and the apparent unsettled volume [$V_0$] is read to the nearest graduated unit. The bulk density is calculated in gram per milliliter [g/ml], by the formula:

$$\rho_{bulk} = \frac{M}{V_0}$$

Tapped Density

The Tapped density was determined according to the United States Pharmacopeia 36 (USP) chapter <616> and European Pharmacopeia (EP) chapter 2.9.15 by mechanically tapping a measuring cylinder containing a powder sample.

Into a 100 ml (readable to 1 mm) cylinder, without compacting, an apparent volume between 50 ml and 100 ml is introduced, weighted [M] with 0.1% accuracy. Carefully the powder sample leveled without compacting, if necessary, and the apparent unsettled volume [$V_0$] is read to the nearest graduated unit.

The cylinder was mechanically tapped containing the sample by raising the cylinder and allowing it to drop under its own weight using a suitable tapped density tester (e.g. JV1000; Fa. Copley) that provides a fixed drop of 3 mm±10% at a nominal rate of 250 drops per minute. The cylinder was initially tapped 500 times and the tapped volume [$V_a$] was measured to the nearest graduated unit. The tapping was repeated for an additional 750 times and the tapped volume [$V_b$] was measured to the nearest graduated unit. If the difference has to be incrementally repeated of 1250 taps, as needed, until the volume difference between succeeding measurements is less than 2%. This final tapped volume [$V_{tapped}$] was considered for the calculation of the tapped density. The tapped density was calculated in gram per milliliter [g/ml], by the formula:

$$\rho_{tapped} = \frac{M}{V_{tapped}}$$

Specific Surface Area

The determination of the specific surface area was performed according to the United States Pharmacopeia 36 (USP) chapter <846> and European Pharmacopeia 7.0 (EP) chapter 2.9.26. The specific surface area is determined utilizing a specific surface area detection equipment (e.g. Quantachrome Nova 2000e BET).

The specific surface area of a powder sample is determined by physical adsorption of a gas (e.g. nitrogen) on the surface of the solid and by calculating the amount of adsorbed gas corresponding to a monomolecular layer on the surface. Physical adsorption results from relatively weak forces (van der Waals forces) between the adsorbed gas molecules and the adsorbent surface of the test powder. The determination is usually carried out at the temperature of liquid nitrogen. The amount of gas adsorbed can be measured by a volumetric or continuous flow procedure.

The specific surface area was measured using the multi-point and single-point determination using the static-volumetric method (Method II).

Prior to the measurement the sample was degassed at 20° C. and vacuum was applied.

Particle Size-/Particle Size Distribution—Measurement Light Diffraction

The determination of the particle size was performed according to the United States Pharmacopeia 36 (USP) chapter <429> and European Pharmacopeia 7.0 (EP) chapter 2.9.31. The particle size distribution was determined utilizing a laser scattering instrument (e.g. Fa. Sympatec GmbH, type HELOS equipped with RODOS dry dispersing unit).

The laser diffraction method is based on the phenomenon that particles scatter light in all directions with an intensity pattern that is dependent on particle size. A representative sample, dispersed at an adequate concentration in a suitable liquid or gas, is passed through the beam of a monochromic light source usually from a laser. The light scattered by the particles at various angles is measured by a multi-element detector, and numerical values relating to the scattering pattern are then recorded for subsequent analysis. The numerical scattering values are then transformed, using an appropriate optical model and mathematical procedure, to yield the proportion of total volume to a discrete number of size classes forming a volumetric particle size distribution (e.g. $d_{50}$ describes a particle diameter corresponding to 50% of cumulative undersize distribution).

Dry samples were transferred into aerosols through the use of powder dispersers, which apply mechanical forces for deagglomeration. The dosing device feeds the disperser with a constant mass flow of sample. The disperser utilizes the energy of compressed gas (e.g. 2 bar) or the differential pressure to a vacuum (e.g. 90-100 mbar) to disperse the particles. The required precision of the method is dependent on characteristics of the sample material (milled versus non-milled, robust vs. fragile). Appropriate measurement conditions are experimentally established, in relation to the desired precision. At least a triplicate detection of representative samples was conducted. The repeatability of the particle size distribution parameter was as follows: for any central value of the distribution (e.g. median $d_{50}$) the coefficient of variation was less than 10%. For values away from the median, (e.g. $d_{10}$ and $d_{90}$) the coefficient of variation did not exceed 15%. Below a particle size of 10 μm the coefficient of variation was doubled.

Particle Size Distribution/Image Analysis

Alternatively, to the laser diffraction method a dynamic image analysis was utilized after qualification with referencing to the light diffraction method. The basic concept is the combination of dry dispersing unit with dynamic image analysis (Fa. Sympatec GmbH, type QICPIC equipped with RODOS/L dry dispersing unit). A representative sample is dry dispersed and the particle flow is led through the image plane. Due to the dispersion the particles are separated from each other by the transportation fluid and overlapping particles are widely avoided.

Dry samples were transferred into aerosols through the use of powder dispersers, which apply mechanical forces for deagglomeration. The dosing device feeds the disperser with a constant mass flow of sample. The disperser utilizes the energy of compressed gas (e.g. 1 bar) or the differential pressure to a vacuum (e.g. 90-100 mbar) to disperse the particles. The required precision of the method is dependent on characteristics of the sample material (milled versus non-milled, robust vs. fragile). Appropriate measurement conditions were experimentally established, in relation to the desired precision. At least a triplicate detection of representative samples was conducted. The repeatability of the particle size distribution parameter was as follows: for any central value of the distribution (e.g. median $d_{50}$) the coefficient of variation was less than 10%. For values away from the median, (e.g. $d_{10}$ and $d_{90}$) the coefficient of variation does not exceed 15%. Below a particle size of 10 μm the coefficient of variation was doubled.

The samples are analyzed using a range module for the DIA sensor of 5-1.705 μm. The calculation of the measured data was performed utilizing the minimum Ferret diameter and "EQPC" mode of the Sympatec QX program package. "EQPC" is the diameter of a circle that has the same area as the projection area of the analyzed particle. The Ferret diameter in general is defined as the distance between the two tangents perpendicular to a particular measuring direction.

Water Content Determination a. Karl Fischer Method/Coulometric Titration

The determination of the water content was performed according to the United States Pharmacopeia 36 (USP) chapter <921> Method Ic and European Pharmacopeia 7.0 (EP) chapter 2.5.32. The Karl Fischer (KF) reaction is used in the coulometric determination of water. Iodine, however, is not added in the form of a volumetric solution but is produced in an iodide-containing solution by anodic oxidation. In the KF oven method, the test substance is heated in a tightly sealed vessel in an oven. The water driven off from the sample is transported into the titration cell with the help of a stream of dry nitrogen gas; there it is determined, usually by means of coulometric KF titration. As reference a standard lactose samples are utilized. Because the sample itself remains in the vessel and only the water enters the titration cell, secondary reactions and matrix effects can be ruled out.

The following determination parameters were utilized for the coulometric KF titration. The blank value was determined in triplicate. The reference was determined with 100-150 mg lactose standard (e.g. Apura Lactose-Standard von Merck, Darmstadt, Art.-Nr. 1.12939). The sample was determined in duplicate with an amount of 0.5-0.6 mg. The oven temperature was adjusted to 150° C., if PEG-Copolymers were determined to 125° C. The nitrogen flow was adjusted at 50-70 ml/min.

The respective number of vials were open conditioned for at least 10 minutes. The vials for system set up and blank value were sealed before the reference samples were weighted into vials and sealed. The prepared vials should not be stored longer than 72 hours. The sample detection was performed according to the equipment manual (e.g. Fa. Methrom KF-Coulometer 756, Fa Metrohm KF-Oven Sample Processor with itrogen connection, Fa Metrohm Dosino 700 and Fa Metrohm Magnetic Stirrer 728).

The analysis of the coulometric detected water content utilized the following equation:

Blank Value $$B = W_B - \left(\frac{Z}{60 \cdot K}\right)$$

B=Blank Value [μg]
K=Drift at the end of the conditioner [μg/min]
$W_B$=Water mass of blank without drift [μg]
Z=Titration time [sec]

Standard Deviation $$SD = \frac{W_S \cdot 100}{S}$$

$W_S$=Determined water content of lactose standard
S=Supplier certified water content lactose standard Water Content $$W_{[\%]} = \frac{\left(W_S - \left(\frac{Z}{60 \cdot K}\right) - B\right) \cdot 100}{10000 \cdot E}$$

$$W_{[ppm]} = \frac{\left(W_S - \left(\frac{Z}{60 \cdot K}\right) - B\right) \cdot 100}{E}$$

W=Water content
$W_S$=Water mass of blank without drift [μg]
Z=Titration time [sec]
E=Weighted sample [g]
B=Blank Value [μg]

The average water content was calculated as average of the duplicate determination. The water content values are expressed herein as % by weight/weight (w/w)

a. Gravimetric/Loss on Drying (LOD)

The water content was determined according to the United States Pharmacopeia 36 (USP) chapter <921> Method and procedure for chemicals—proceed as directed in the individual monograph preparing the chemical as directed under Loss on Drying (LOD)<731> and also according European Pharmacopeia 7.0 (EP) chapter 2.2.32. However, this method suffers from the drawback that it determines not only the water content, but also other volatile constituents in the sample The detection of the water content via gravimetric method was performed with a halogen moisture analyzer (e.g. Fa. Mettler Toledo, Type HG63). This kind of equipment is working according to the thermo-gravimetric principle. That means the water content is analyzed via the surrogate parameter of detected weight loss while heating a water containing sample.

At the beginning of the detection the sample was placed on an aluminum bowl and the net weight of the sample was detected considering the tare weight of the aluminum bowl. If the sample shows a mean particle size more than 2 mm the sample should be crushed, however, avoiding too much energy uptake of the sample to avoid water loss during the sample preparation. The required sample weight depends on the desired deviation of the reproducibility.

| Reproducibility of Results | Minimum sample Weight |
|---|---|
| ±0.02% | 10 g |
| ±0.05% | 4 g |
| ±0.1% | 2 g |
| ±0.2% | 1 g |

Then, the sample was be heated up to 110° C. and kept at this temperature during the detection period utilizing the halogen heating module of the halogen moisture analyzer. The moisture will volatile and the precision balance will detect a sample weight loss. The sample was dried until a constant mass was observed as predefined by a sample weight loss of less than 1 mg per 50 sec (e.g. Fa. Mettler Toledo, Type HG63; switch off criteria 3).

The analysis of the gravimetric detected water content utilized the following equation:

$$MC = \frac{m_w - m_D}{m_w} \cdot 100$$

$$DC = \frac{m_D}{m_w} \cdot 100$$

$MC$ = Content of volatile constituents [%]

$DC$ = Dry content [%]

$m_w$ = Wet sample mass [g]

$m_d$ = Dry sample mass [g]

The water content values are expressed herein as % by weight/weight (w/w)

Inherent Viscosity (IV)

The determination of the inherent viscosity was performed in a Ubbelohde viscometer of type 0c at 25±0.1° C. utilizing a sample concentration of 0.1% dissolved in chloroform. The inherent viscosity represents the ratio of the natural logarithm of the relative viscosity $[\eta_r]$ to the mass concentration of the polymer [c]. The quantity $[\eta_{in}]$ with which the inherent viscosity is synonymous is the logarithmic viscosity number.

$$\eta_{IV} \equiv \eta_{in} = \frac{\ln \eta_r}{c}$$

100±5 mg sample was introduced into a 100 ml graduated flask. The graduated flask was filled with approximately 9/10 chloroform and a ferrite stir bar was immersed. The sample was dissolved while stirring with the ferrite stir bar utilizing a rotating magnetic field (magnetic stirrer). The ferrite stir bar rotation speed was appropriately adjusted with regard to the stir bar dimensions and the sample characteristics. Samples with an expected IV of not more than 1 dl/g were stirred for at least 6 hours and samples with an expected IV equal or more than 1 dl/g were stirred for at least 12 hours to ensure the dissolution of the samples in chloroform. After the respective stirring period the ferrite stir bar was removed, the graduated flask was filled to the calibration mark with chloroform and the stir bar was immersed again. Afterwards, the sample was stirred for additional 15 minutes to ensure homogeneity of the sample.

In order to determine the down time of the Uppelohde viscometer filtrated chloroform was introduced into a clear and dry viscometer. The maximum volume (approximately 15 ml) is indicated by a mark. The determination of the down time was conducted with a triplicate determination of the retention time.

In order to determine the retention time of the sample the prepared and filtrated sample solution was introduced into the clean and dried Uppelohde viscometer. The determination of the filtrated sample solution was conducted in a triplicate. Samples with an expected IV not more than 0.24 dl/g were determined in different Uppelohde viscometers (e.g. 2 samples solution=4 single determinations=4 viscometer) in order to avoid outlier. The determined retention times equipment related was corrected according to the "Hagenbach" correction for DIN-viscometer (DIN 51562 part 3).

$$t = \frac{x}{Z^2}$$

$$x = \frac{2.49}{K \cdot \sqrt{K \cdot \frac{\sqrt[4]{(K*16.37375)}}{10}}}$$

For estimating the "Hagenbach" correction the following equation could be utilized with sufficient precision.

$$t = \frac{E}{K \cdot Z^2}$$

$$E = \frac{C}{K^{5/8}}$$

$t$ = time correction [sec]

$Z$ = average retention time [sec]

$K$ = capillary constant of the utilized viscometer $C$ = 5.59576 (for micro capillary 0.2331655)

The calculation of the IV the following equation will be utilized:

$$IV = \frac{\ln\frac{T}{T_0}}{c} = \frac{\ln\frac{Z_{sample} - t_{sample}}{Z_{solvent} - t_{solvent}}}{c}$$

$IV$ = inherent viscosity [dl/g]

$T$ = corrected sample retention time [sec]

$Z_{sample}$ = retention time sample [sec]

$t_{sample}$ = time correction [sec]

$T_0$ = corrected solvent retention time [sec]

$Z_{solvent}$ = retention time solvent [sec]

$t_{solvent}$ = time correction solvent [sec]

$c$ = concentration sample solution

Glass Transition Temperature/Differential Scanning Calorimetry (DSC)

The different glass transition temperatures was determined according to the United States Pharmacopeia 36 (USP) chapter <891>, European Pharmacopeia 7.0 (EP) chapter 2.2.34 and more specific to DIN 53765:1994-03 (D).

DIN 53765:1994-03 (D) is defining the glass transition temperature more in detail: The glass transition is a reversible transition from a hard and relatively brittle, frozen state to a molten or rather rubbery state within amorphous or partly amorphous materials.

During the glass transition, numerous material properties as Young's modulus, specific heat capacity and the coefficient of thermal expansion are changing considerably faster (escalades) in comparison to the temperature range below and above.

The glass transition temperature is determined utilizing a Differential Scanning calorimeter (e.g. Fa. Netzsch; type DSC 200 PC). The aluminum sample pan (e.g. 25/40 μl) with perforated lid considering are tarred before approximately 5 mg sample are introduced. Afterward, the aluminum pan and lid are cold sealed. The first heating circle is introduced with a heat rate of 10K/min starting at 20° C. up to 150° C. under nitrogen atmosphere. Afterwards, the sample is cooled to −20° C. with a cooling rate of 10K/min before the second heating circle is started with a heating rate of 10K/min up to 150° C. The cooling temperature before the second heating cycle should be 50K below the expected glass transition temperature. The glass transition temperature is determined in the second heating run. Possibly observed peaks in the first heating circle are considered as relaxation peaks and, therefore, are not evaluated such peaks disappear in the second heating circle.

The temperature range where the glass transition occurs is defined as glass transition range. The glass transition is characterized utilizing the glass transition temperature ($T_g$) at which 50% of the change in specific heat capacity is reached. For further characterization of the glass transition range the following temperatures are also defined:

The glass transition onset temperature ($T_{gO}$) and the glass transition extrapolated onset temperature ($T_{gO}^E$)

The Glass transition end temperature ($T_{gE}$) and the glass transition extrapolated end temperature ($T_{gE}^E$)

The difference ΔT between the glass transition extrapolated onset temperature ($T_{gO}^E$) and glass transition Extrapolated End temperature ($T_{gE}^E$) is also defined.

Acid Value

The determination of the acid value is conducted utilizing potentiometric titration with tetra-n-butylammonium hydroxide (TBAH) solution, c=0.1 mol/l via dynamic equivalence point titration (DET). The sample will dissolved in 60 ml of a solvent mixture of 73% v/v chloroform (quality pro analysis [p.A]), 13.5% v/v dioxan (quality p.A.) and 13.5% v/v methanol (quality p.A.) while gentle stirring for a maximum of 30 minutes. For samples with an expected acid value lower than 1 mg KOH/g an amount of 1.5-3 g is introduced into the solvent mixture and for samples with an expected acid value of more than 1 mg KOH/g an amount of 1.0-3 g is introduced into the solvent mixture considering a minimum consumption of 0.3 ml TBAH. The determination is conducted in the solvent mixture via potentiometric titration of the acid protons with TBAH. Before determining the sample solution the titer and the blank value of the solvent mixture is determined in duplicate. Afterwards, the sample will be determined at least in duplicate and the mean acid value is calculated.

The analysis of the acid value utilizes the following equation:
1 ml TBAH solution (c=0.1 mol/l) is equal to 5.611 mg KOH/g sample weight.

$$SZ = \frac{(V_P - V_{BL}) \cdot T \cdot M_{KOH}}{E_P}$$

$SZ$ = acid value [mg KOH/g]

$V_P$ = consumption TBAH [ml]

$V_{BL}$ = consumption TBAH for blank value [ml]

$T$ = titer TBAH $M_{KOH}$ = molar weight KOH (g/mol)

$E_P$ = sample weight (g)

Examples 1-4

As a bio-resorbable polymer a Poly(D,L-lactide-co-glycolide) 50:50 with an inherent viscosity of 0.2 and an acid end group was chosen (RESOMER® RG 502 H) for examples 1 to 4. The polymer was dissolved in acetone (step a) and then precipitated by the addition of an excess of water to form a wet polymer mass (step b). The precipitated polymer mass suspension was mechanically pressed in order to reduce excess water. The water content of the wet polymer mass was around 90% (w/w). After the mechanical pressing the wet polymer mass was transferred into a fluid bed equipment (e.g. Glatt GPCG 3.1). The polymer mass was pre-dried in the fluid bed equipment with a constant inlet air flow and product temperature (step c). After approximately 90 minutes the pre-dried polymer mass (with an LOD of 35-60% w/w) was comminuted by being passed through a 2 mm screen (e.g. manually or utilizing a sieving apparatus) to give polymer particles (step d). These polymer particles were dried in the fluid bed equipment with a constant inlet air flow and temperature until the LOD of ≤0.5% w/w is achieved (step e). Subsequently the dried polymer particles of examples 1 to 3 were post-treated in the fluid bed equipment with a constant inlet air flow and product temperature (step f). In the case of comparative example 4 step e was prolonged instead of a post-treatment. After the post treatment the polymer particles of examples 1 to 3 were milled utilizing a jet mill resulting in a particle size distribution of $d_{50}$ of 27 µm or less and $d_{90}$ of 57 µm or less (step g).

The Glass transition temperatures of the bio-resorbable polymer of examples 1 to 4 are:

| $T_{gO}$ [° C.] | $T_{gO}^E$ [° C.] | $T_g$ [° C.] | $T_{gE}^E$ [° C.] | $T_{gE}$ [° C.] |
|---|---|---|---|---|
| 38.2 | 42.6 | 44.1 | 45.7 | 51.2 |

TABLE 2

Drying step e

| | Example: | | | |
|---|---|---|---|---|
| | 1 | 2 | 3 | 4 comparative |
| Fluid bed equipment | Glatt GPCG 3.1 | | | |
| Exhaust air filter system | Filter socks/20 µm Baskets | | | |
| Filter cleaning interval [sec] | 5 | | | |
| Filter cleaning time [sec] | 5 | | | |
| Inlet air volume [m³/h] | 66-205 | 100-200 | 100-200 | 99-200 |
| Inlet air temperature [° C.] | 35.0-35.6 | 34.9-35.5 | 33.7-35.2 | 34.8-35.3 |
| Exhaust air temperature [° C.] | 23.6-33.0 | 20.9-32.8 | 21.3-33.6 | 20.5-34.3 |
| Product bed temperature [° C.] | 21.2-34.6 | 19.7-34.6 | 19.8-34.0 | 19.3-34.6 |
| Process time [min] | 270 | 225 | 270 | 960 |
| Process start LOD [% w/w] | 64.08 | 68.71 | 73.95 | 69.0 |
| Process end LOD [% w/w] | 0.46 | 0.40 | 0.49 | 0.44 |
| Yield [%] | | | | 89.49 |

TABLE 3

Post treatment (step f)

| | Example: | | | |
|---|---|---|---|---|
| | 1 | 2 | 3 | 4 comparative |
| Fluid bed equipment | Glatt GPCG 3.1 | | | |
| Exhaust air filter system | Filter socks/20 µm Baskets | | | |
| Filter cleaning interval [sec] | 5 | | | |
| Filter cleaning time [sec] | 5 | | | |
| Inlet air volume [m³/h] | 148-164 | 160 | 160 | — |
| Inlet air temperature [° C.] | 55-58 | 50 | 46-49 | — |
| Exhaust air temperature [° C.] | 42-45 | 45-46 | 42-44 | — |
| Product bed temperature [° C.] | 48-49 | 45-46 | 43-44 | — |
| Process time [min] | 10 | 30 | 40 | — |
| Cooling @ 35° C. [min] | 10 | 10 | 10 | — |
| Yield [%] | 77.71 | 92.77 | 96.81 | — |

TABLE 4

Milling (step g)

| | Example: | | |
|---|---|---|---|
| | 1 | 2 | 3 |
| Milling equipment | Hosokawa Alpine Jet Mill AFG 100 | | |
| Nozzle [mm] | 1.9 | 1.9 | 1.9 |
| Classifier type | Standard | Standard | Standard |
| Classifier speed [rpm] | 3.600 | 3.600 | 3.600 |
| Throughput [kg/h] | 2.1 | 2.1 | 1.6 |
| Pressure [bar] | 6.0 | 6.0 | 6.0 |

The material gained from example 4 was not milled.

TABLE 4

Parameters of intermediate and end products from the examples 1-4

| Example | Time [min] | Process | Particle size [µm] | | | LOD [% w/w] | Density [g/ml] | |
|---|---|---|---|---|---|---|---|---|
| | | | $d_{10}$ | $d_{50}$ | $d_{90}$ | | Bulk | Tapped |
| 1 | 270 | Drying (step e) | — | — | <2000 | 0.46 | 0.31 | 0.36 |
| | 10 | Post-treatment (step f) | — | 413.9 | 881.25* | — | 0.58 | 0.69 |
| | n/a | Milling (step g) | 6.5 | 22.5 | 39.02 | — | 0.59 | 0.59 |
| 2 | 225 | Drying (step e) | — | — | <2000 | 0.46 | 0.33 | 0.40 |
| | 30 | Post-treatment (step f) | — | 381.3 | 846.48* | 0.18 | 0.46 | 0.55 |
| | n/a | Milling (step g) | 5.8 | 20.4 | 38.93 | — | 0.42 | 0.57 |
| 3 | 270 | Drying (step e) | — | — | <2000 | 0.46 | 0.34 | 0.40 |
| | 40 | Post-treatment (step f) | — | 292.1 | 833.09* | 0.24 | 0.45 | 0.54 |
| | n/a | Milling (step g) | 5.9 | 20.7 | 38.35 | — | 0.41 | 0.54 |
| 4 (comparative) | 480 | Drying (step e) | — | — | <2000 | 0.42 | 0.28 | 0.31 |
| | 750 | Drying (step e) | — | — | <2000 | 0.37 | 0.27 | 0.33 |
| | 960 | Drying (step e) | — | — | <1000 | 0.44 | 0.28 | 0.35 |

*$d_{97}$

Example 4 shows that the prost-treatment step f) cannot be substituted by prolonging the drying step e. The material gained from example 4 shows in comparison to examples 1-3 shows a low bulk and tapped density which is supposed to be caused by a higher rate of inclusion of micropores in the polymer material. Electron microscopic pictures of the polymer materials verify this assumption.

Storage Stability

The powder material of comparative example 5 was gained similar to comparative example 4 with the exception that the drying step was performed in a streaming tube instead of a fluid bed equipment and that the polymer was comminuted to a powder. In tables 5 to 7 the storage stability was compared to the powder material from example 1 and 3.

TABLE 5

Storage stability of comparative example 5

| Comparative Example 5 | Storage | Acid value [mg KOH/g] | Inherent viscosity [dl/g] | Water content (KF) [% w/w] | BET* [m$^2$/g] |
|---|---|---|---|---|---|
| Poly(D,L-lactide-co-glycolide) 50:50, acid end group | before storage | 9.6 | 0.22 | 0.38 | 13.058 |
| | 24 h/ 30° C. | 9.5 | 0.21 | 0.51 | 13.167 |
| | 48 h/ 30° C. | 9.4 | 0.21 | 0.67 | — |
| | 72 h/ 30° C. | 9.4 | 0.22 | 0.62 | — |
| | 96 h/ 30° C. | 9.4 | 0.21 | 0.46 | 6.449 |
| | 4 weeks/ 30° C. | 9.1 | 0.21 | 0.44 | 2.850 |

TABLE 6

Storage stability of the bio-degradable powder material from example 1

| Example | Storage | Acid value [mg KOH/g] | Inherent viscosity [dl/g] | Water content (KF) [% w/w] | BET* [m$^2$/g] |
|---|---|---|---|---|---|
| 2 | before storage | 10.5 | 0.21 | 0.325 | 0.552 |
| | 24 h/ 30° C. | 10.6 | 0.19 | 0.265 | 0.167 |
| | 48 h/ 30° C. | 10.6 | 0.19 | 0.205 | — |
| | 72 h/ 30° C. | 10.6 | 0.2 | 0.245 | 0.438 |
| | 96 h/ 30° C. | 10.6 | n/a | 0.24 | 0.348 |
| | 1 week/ 30° C. | 10.6 | n/a | 0.235 | 0.295 |
| | 2 weeks/ 30° C. | 10.7 | 0.2 | 0.185 | 0.253 |
| | 4 weeks 30° C. | 10.7 | 0.2 | 0.275 | 0.245 |

TABLE 7

Storage stability of the bio-degradable powder material from example 3

| Example | Storage | Acid value [mg KOH/g] | Inherent viscosity [dl/g] | Water content (KF) [% w/w] | BET* [m$^2$/g] |
|---|---|---|---|---|---|
| 3 | before storage | 10.5 | 0.21 | 0.255 | 0.606 |
| | 24 h/30° C. | 10.6 | 0.19 | 0.25 | n/a |
| | 48 h/30° C. | 10.5 | 0.2 | 0.205 | 0.260 |
| | 72 h/30° C. | 10.6 | 0.2 | 0.23 | 0.278 |
| | 96 h/30° C. | 10.6 | 0.2 | 0.23 | 0.292 |
| | 1 week/ 30° C. | 10.6 | 0.2 | 0.225 | 0.248 |
| | 2 weeks/ 30° C. | 10.7 | 0.19 | 0.185 | 0.171 |
| | 4 weeks/ 30° C. | 10.7 | 0.2 | 0.275 | 0.143 |

Table 7:
*)BET expresses the specific surface area (BET method)

Result: The powder material of comparative example 5 has an extremely high specific surface area and is less storage stable the powder material that from example 2 and from example 3.

The invention claimed is:

1. A process for preparing a bio-resorbable polyester in the form of a powder, wherein the bio-resorable polyester has
    a bulk density of 0.3 g/ml or more,
    a tapped density of 0.4 g/ml or more and
    a specific surface area of 2.0 m$^2$/g or less
    the process comprising:
    (a) dissolving a bio-resorbable polyester in a first solvent to form a polymer solution,
    (b) contacting the polymer solution with a second solvent to result the precipitation of the bio-resorbable polyester in the form of a wet polymer mass, wherein said second solvent comprises water or is a mixture of more than 50% water and the balance of a water soluble solvent,
    (c) pre-drying the wet polymer mass at a temperature below the $T_{gO}$ of the bio-resorbable polyester,
    (d) comminuting the pre-dried polymer mass to polymer particles with a size below 10 mm,
    (e) drying the comminuted polymer particles at a temperature below the $T_{gO}$ of the bio-resorbable polyester to a residual water content of 1% or less by weight/weight,
    (f) performing post-treatment of the polymer particles from the drying (e) at a temperature in the range from the $T_{gO}$ to the $T_{gE}$ of the bio-resorbable polyester, and
    (g) comminuting the polymer particles from the post-treatment (f) to a powder with a particle size of $d_{50}$ of 1-300 μm and $d_{90}$ of more than 30 and up to 3000 μm.

2. The process according to claim 1, wherein the bio-resorbable polyester is a polylactic acid, a polyglycolic acid, a poly-caprolactone, a lactic acid-glycolic acid copolymer, a lactic acid-glycolic acid-polyethylene blockcopolymer, a lactic acid-glycolic acid-caprolactone terpolymer, a lactic acid-caprolactone copolymer, a poly dioxanone or a lactic acid-trimethylene carbonate copolymer or any blend of the polymers.

3. The process according to claim 1, wherein the bio-resorbable polyester is a poly(D,L-lactide-co-glycolide) copolymer with an inherent viscosity from 0.1-2.0.

4. The process according to claim 3, wherein the proportion of D,L-lactide to glycolide in the poly(D,L-lactide-co-glycolide) copolymer is from 70:30 to 30:70 parts by weight.

5. The process according to claim 1, wherein the second solvent is a mixture of more than 60% water and the balance of a water soluble solvent.

6. The process according to claim 1, wherein the second solvent is a mixture of more than 70% water and the balance of a water soluble solvent.

7. The process according to claim 1, wherein the second solvent is a mixture of more than 80% water and the balance of a water soluble solvent.

8. The process according to claim 1, wherein the second solvent is a mixture of more than 90% water and the balance of a water soluble solvent.

9. The process according to claim 1, wherein the polymer mass in the pre-drying (c) is dried to a residual water content measured as loss on drying from 30 to 70% by weight/weight.

10. The process according to claim 1, wherein at least one of the pre-drying (c), the drying (e), or the post-treatment (f) are performed in a fluidized bed drying equipment.

11. The process according to claim 1, wherein the polymer particles in the post-treatment (f) are dried at a temperature in a range from the $T_{gO}$ to the $T_{gE}^{E}$ of the bio-resorbable polyester.

12. The process according to claim 1, wherein the polymer particles in the post-treatment (f) are dried to a residual water content measured by the Karl Fischer method of 0.5% or less by weight/weight.

* * * * *